(12) United States Patent
Rathjen et al.

(10) Patent No.: US 12,303,433 B2
(45) Date of Patent: May 20, 2025

(54) OPHTHALMOLOGICAL DEVICE FOR REFRACTIVE CORRECTION OF A CORNEA

(71) Applicant: Ziemer Ophthalmic Systems AG, Port (CH)

(72) Inventors: Christian Rathjen, Bremen (DE); Michael Steinlechner, Zurich (CH)

(73) Assignee: Ziemer Ophthalmic Systems AG, Port (CH)

( * ) Notice: Subject to any disclaimer, the term of this patent is extended or adjusted under 35 U.S.C. 154(b) by 250 days.

(21) Appl. No.: 17/718,637

(22) Filed: Apr. 12, 2022

(65) Prior Publication Data

US 2022/0331163 A1    Oct. 20, 2022

(30) Foreign Application Priority Data

Apr. 19, 2021   (CH) .................................... 00407/21

(51) Int. Cl.
*A61F 9/008*    (2006.01)
*A61F 9/009*    (2006.01)

(52) U.S. Cl.
CPC ...... *A61F 9/00804* (2013.01); *A61F 9/00814* (2013.01); *A61F 9/009* (2013.01);
(Continued)

(58) Field of Classification Search
CPC .. A61F 9/00804; A61F 9/00814; A61F 9/009; A61F 2009/00872; A61F 2009/00897
See application file for complete search history.

(56) References Cited

U.S. PATENT DOCUMENTS

2006/0106372 A1* 5/2006 Kuhn ...................... A61F 9/008
606/5
2007/0179483 A1* 8/2007 Muhlhoff ................ A61F 9/008
606/4
(Continued)

FOREIGN PATENT DOCUMENTS

EP    0657151 A1    6/1995
EP    1981454 B1    5/2020

OTHER PUBLICATIONS

Walter Sekundo et al, "Small Incision Lenticule Extraction (SMILE): principles, techniques, complication management, and future concepts." Cham, Switzerland: Springer, 2015. Print. viewed on Mar. 30, 2024.*
(Continued)

*Primary Examiner* — Catherine M Voorhees
*Assistant Examiner* — James Moss
(74) *Attorney, Agent, or Firm* — Banner & Witcoff, Ltd.

(57) ABSTRACT

An ophthalmological device for refractive correction of a cornea comprises a laser source, a focusing optical module, a scanner system and an electronic circuit. The electronic circuit is configured to control the scanner system to move the focal spot of the pulsed laser beam generated by the laser source to generate a first part of a void volume ablating cornea tissue inside the first part of the void volume, and to generate a separated second part of the void volume by separating the second part of the void volume as piece of cornea tissue to be removed from the void volume through an incision in the cornea, whereby at least a part of the separated second part is separated from the cornea by the ablated first part.

14 Claims, 5 Drawing Sheets

(52) U.S. Cl.
CPC ............... *A61F 2009/00872* (2013.01); *A61F 2009/00897* (2013.01)

(56) References Cited

U.S. PATENT DOCUMENTS

| | | | | |
|---|---|---|---|---|
| 2007/0282312 | A1* | 12/2007 | Rathjen | A61F 9/00825 606/4 |
| 2008/0077121 | A1 | 3/2008 | Rathjen | |
| 2010/0094264 | A1* | 4/2010 | Rathjen | A61F 9/009 606/4 |
| 2010/0331831 | A1* | 12/2010 | Bischoff | A61F 9/00804 606/5 |
| 2015/0250652 | A1* | 9/2015 | Holliday | A61F 9/00827 606/5 |
| 2015/0305928 | A1* | 10/2015 | Stobrawa | A61F 9/00836 606/5 |
| 2016/0374857 | A1* | 12/2016 | Fu | A61F 9/0084 606/3 |
| 2018/0000647 | A1* | 1/2018 | Malek Tabrizi | A61B 3/0008 |
| 2019/0015251 | A1* | 1/2019 | Rathjen | A61F 9/0084 |
| 2020/0368065 | A1* | 11/2020 | Bischoff | A61F 9/00836 |
| 2022/0192870 | A1* | 6/2022 | Steinlechner | A61F 9/008 |
| 2023/0015597 | A1* | 1/2023 | Rathjen | A61F 9/008 |

OTHER PUBLICATIONS

Yan Quan et al. Femtosecond Laser-Assisted Ophthalmic Surgery: From Laser Fundamentals to Clinical Applications. Micromachines. 2022; 13(10):1653. https://doi.org/10.3390/mi13101653, viewed on Mar. 30, 2024.*

H. Kaz Soong et al., Femtosecond Lasers in Ophthalmology, American Journal of Ophthalmology, vol. 147, Issue 2, 2009, pp. 189-197.e2, ISSN 0002-9394, https://doi.org/10.1016/j.ajo.2008.08.026. Viewed on Oct. 8, 2024—see Table Lasers in Opthamology (Year: 2009).*

Alice Zhang et al. Laser Principles in Ophthalmology. [Updated Aug. 25, 2023]. In: StatPearls [Internet]. Treasure Island (FL): StatPearls Publishing; Jan. 2024. https://www.ncbi.nlm.nih.gov/books/NBK582153/. viewed on Oct. 8, 2024 (Year: 2024).*

Aug. 18, 2021—(CH) Search Report—App No. 4072021.

* cited by examiner

OPHTHALMOLOGICAL DEVICE FOR REFRACTIVE CORRECTION OF A CORNEA

CROSS-REFERENCE TO RELATED APPLICATION

The present application claims priority to and the benefit of Switzerland Patent Application 00407/21 filed Apr. 19, 2021, which is incorporated by reference in its entirety herein.

FIELD OF THE DISCLOSURE

The present disclosure relates to an ophthalmological device for refractive correction comprising a laser source for generating a pulsed laser beam, a focusing optical module for converging the pulsed laser beam onto a focal spot in the cornea, and a scanner system for moving the focal spot to target locations in the cornea for generating a void volume inside the cornea for refractive correction of the cornea.

BACKGROUND OF THE DISCLOSURE

For the purposes of working on eye tissue by means of a laser beam, a work region is scanned by laser pulses by virtue of the pulsed laser beam being deflected in one or more scan directions by means of suitable scanner systems. In general, movable mirrors are used to deflect the light beams and/or the laser pulses, for example femtosecond laser pulses, said movable mirrors being pivotable about one or two scan axes, for example by way of galvano scanners, piezo scanners, polygon scanners, or resonance scanners.

U.S. Pat. No. 7,621,637 describes an apparatus for working on eye tissue, said apparatus having a base station with a laser source for producing laser pulses and a scanner, arranged in the base station, with movable deflection mirrors for deflecting the laser pulses in a scan direction. The deflected laser pulses are transferred via an optical relay system from the base station to an application head, the latter passing over a work region according to a scan pattern by means of a mechanically moved projection optical unit. According to U.S. Pat. No. 7,621,637, in the application head, the deflection in the scan direction, which is much faster in comparison with the mechanical movement, is overlaid onto the mechanical movement of the projection optical unit and consequently onto the scan pattern thereof. A fast scanner system in the base station facilitates a fine movement of the laser pulses (micro-scan), which is overlaid on the scan pattern of the movable projection optical unit that covers a large work region, for example the entire eye.

For refractive correction, pulsed laser radiation is used in corneal surgery to create a lenticule inside the cornea. To achieve the refractive correction, the created lenticule is subsequently removed from the cornea through one or more extraction channels cut in the cornea. US 2016/0089270 describes a system and a method for cutting lenticules in the eye tissue. According to US 2016/0089270, straight-lined fast scan lines are overlaid to this end on slower work lines that are traced out along meridians of the lenticule.

Theoretically, the exact form, including shape and size, of the lenticule to be removed for refractive correction of the cornea can be determined using standard optical lens formulas, which produce zero thickness at the border (for myopic corrections) or at the center (for hyperopic corrections). However, cutting these shapes directly into the cornea produces unstable lenticules which are hard to manipulate by the surgeon and, owing to the extreme thinness of their central or peripheral areas, have a propensity of at least partially ripping during the extraction. Moreover, the corneal stroma bed is structured in lamely (collagen layers) with a thickness of approximately 2 µm. Cutting structures which are close to this scale thus often produces frayed edges. The partial tears and frayed edges make it difficult for a surgeon to judge whether the lenticule was indeed extracted successfully in its entirety from the patient's eye.

EP 2211804 describes an apparatus for operatively correcting myopia or hyperopia in an eye by emitting laser radiation into the cornea to cut a lenticule which is removed from the cornea for the desired refractive correction. To avoid the aforementioned problems of partial tears and frayed edges, EP 2211804 teaches to cut the lenticule with a minimum thickness in the range of 5 µm to 50 µm at the edge of the lenticule for correction of myopia and in the region of the axis of vision for correction of hyperopia. Nevertheless, increasing the thickness of the lenticule goes hand in hand with an undesirable enlargement of the lenticular cornea tissue which is removed from the cornea. While the enlargement of the lenticular improves its structural stability, it unnecessarily weakens the cornea itself and partly counteracts the minimally invasive nature of the lenticule extraction procedure.

SUMMARY OF THE DISCLOSURE

The present disclosure proposes an ophthalmological device for refractive correction of a cornea of an eye using a pulsed laser beam, which device does not have at least some of the disadvantages of the prior art. Particularly, the present disclosure proposes an ophthalmological device for refractive correction of a cornea which reduces the risk for tearing of a lenticule to be extracted from the cornea while avoiding unnecessary weakening of the cornea.

According to the present disclosure, advantages are achieved by the features of the independent claims. Moreover, further advantageous embodiments emerge from the dependent claims and the description.

An ophthalmological device for refractive correction of a cornea of an eye, by generating a void volume inside the cornea, comprises: a laser source configured to generate a pulsed laser beam; a focusing optical module configured to make the pulsed laser beam converge onto a focal spot in the cornea; a scanner system configured to move the focus to target locations in the cornea; and an electronic circuit configured to control the scanner system.

According to the present disclosure, the above-mentioned features are particularly achieved in that the electronic circuit is configured to control the scanner system to move the focal spot inside the cornea to generate an ablated first part of the void volume by ablating cornea tissue with a thickness of more than one focal spot inside the first part of the void volume, and to generate a separated second part of the void volume by separating the second part of the void volume as piece of cornea tissue to be removed from the void volume through an incision in the cornea, whereby at least a part of the separated second part is separated from the cornea by the ablated first part.

In an embodiment, the electronic circuit is configured to control the scanner system to move the focal spot inside the cornea to cut the anterior volume surface of the void volume, and to control the scanner system to move the focal spot inside the cornea to ablate the cornea tissue between the second part of the void volume and the posterior volume surface of the void volume.

In an embodiment, the electronic circuit is configured to control the scanner system to move the focal spot inside the cornea to ablate the cornea tissue in the first part of the void volume and thereby shape the piece of cornea tissue in the second part of the void volume.

In an embodiment, the electronic circuit is configured to control the scanner system to move the focal spot inside the cornea to ablate the cornea tissue in the first part of the void volume and generate the piece of cornea tissue in the second part of the void volume in shape of a lenticule.

In an embodiment, the electronic circuit is configured to control the scanner system to move the focal spot inside the cornea to ablate the cornea tissue in the first part of the void volume and generate the piece of cornea tissue in the second part of the void volume with a ring shape.

In an embodiment, the electronic circuit is configured to control the scanner system to move the focal spot inside the cornea to ablate the cornea tissue in the first part of the void volume and thereby shape the piece of cornea tissue in the second part of the void volume with a rounded rim.

In an embodiment, the electronic circuit is configured to control the scanner system to move the focal spot inside the cornea to ablate the cornea tissue in the first part of the void volume and thereby shape the piece of cornea tissue in the second part of the void volume with a rim having a straight wall in direction of an optical axis of the focusing optical module.

In an embodiment, the electronic circuit is configured to control the scanner system to move the focal spot inside the cornea to ablate the cornea tissue in the first part of the void volume and thereby shape the ablated first part of the void volume with a rim having a straight wall in direction of an optical axis of the focusing optical module.

In an embodiment, the ophthalmological device further comprises a patient interface with a contact body, which contact body brings an exterior surface of the cornea in an applanated form in a state where the patient interface is applied on the cornea; and the electronic circuit is configured to control the scanner system to move the focal spot inside the cornea to cut the anterior volume surface of the void volume equidistant to the exterior surface of the cornea.

In an embodiment, the scanner system comprises a first scanner device configured to move the focal spot with a first scanning speed to target locations along a working line, and a second scanner device configured to move the focal spot with a second scanning speed, comparatively faster than the first scanning speed, to target locations along a scan line which runs through the working line at an angle to the working line; and the electronic circuit is configured to control the first scanner device to move the focal spot to target locations along a spiral shaped working line inside the cornea, and to control the second scanner device to move the focal spot to target locations along the scan line to ablate the cornea issue and generate the ablated first part of the void volume.

In an embodiment, the scanner system comprises a divergence modulator configured to modulate a divergence of the pulsed laser beam for adjusting a location of the focal spot along an optical axis of the focusing optical module and tilting the scan line in direction of the optical axis; and the electronic circuit is configured to control the divergence modulator to adjust a tilting angle of the scan line with respect to a shape of the ablated first part and/or the separated second part.

In an embodiment, the scanner system comprises a length modulator configured to modulate a length of the scan line; and the electronic circuit is configured to control the length modulator to adjust the length of the scan line with respect to a shape of the ablated first part and/or the separated second part.

In an embodiment, the electronic circuit is configured to control the laser source to adjust one or more parameters of the pulsed laser beam for ablating different regions of the ablated first part with different parameters of the pulsed laser beam, whereby the one or more parameters of the pulsed laser beam include pulse energy, pulse overlap, pulse rate, pulse duration, and/or focal spot size.

In an embodiment, the electronic circuit is configured to control the laser source to adjust one or more parameters of the pulsed laser beam for processing a region of corneal tissue adjacent to at least part of the outer surface of the piece of cornea tissue to be removed from the void volume to fuse the corneal tissue of the part of the outer surface of the piece of cornea tissue. The one or more parameters of the pulsed laser beam include pulse energy, pulse overlap, pulse rate, pulse duration, and/or focal spot size.

In an embodiment, the electronic circuit is configured to include in the first part of the void volume any area of the void volume which has a thickness smaller than a defined thinness threshold.

In an embodiment, the electronic circuit is configured to control the scanner system to move the focal spot inside the cornea to ablate the cornea tissue in any area of the void volume which has a thickness smaller than a defined thinness threshold, without extracting any corneal tissue from this area.

In addition to the ophthalmological device for refractive correction of a cornea of an eye, the present disclosure further relates to a computer program product, particularly, a computer program product comprising a non-transitory computer-readable medium having stored thereon computer program code for controlling a processor of an ophthalmological device for refractive correction of a cornea of an eye by generating a void volume inside the cornea. The ophthalmological device comprises a laser source configured to generate a pulsed laser beam, a focusing optical module configured to make the pulsed laser beam converge onto a focal spot in the cornea, and a scanner system configured to move the focal spot to target locations in the cornea. The computer program code is configured to control the processor such that the processor directs the scanner system to move the focal spot inside the cornea to generate an ablated first part of the void volume by ablating cornea tissue with a thickness of more than one focal spot inside the first part of the void volume, and to generate a separated second part of the void volume by separating the second part of the void volume as piece of cornea tissue to be removed from the void volume through an incision in the cornea, whereby at least a part of the separated second part is separated from the cornea by the ablated first part.

In an embodiment, the computer program product has further computer program code stored on the computer-readable medium and configured to control the processor such that the processor controls the scanner system to move the focal spot inside the cornea to ablate the cornea tissue in the first part of the void volume and thereby shape the piece of cornea tissue in the second part of the void volume.

In another aspect, the present disclosure relates to an ophthalmological device for refractive correction of a cornea of an eye, which ophthalmological device comprises: a laser source configured to generate a pulsed laser beam; a focusing optical module configured to make the pulsed laser beam converge onto a focal spot in the cornea; a scanner system configured to move the focus to target locations in the cornea; and an electronic circuit configured to control the scanner system to generate a lenticule or ring inside the cornea for removal through an incision in the cornea; wherein the electronic circuit is further configured to control the laser source to adjust one or more parameters of the pulsed laser beam for processing a region of corneal tissue adjacent to at least part of the outer surface of the lenticule or ring to fuse the corneal tissue of the part of the outer surface of the lenticule or ring. The one or more parameters of the pulsed laser beam include pulse energy, pulse overlap, pulse rate, pulse duration, and/or focal spot size. For fusing the corneal tissue, the parameters of the pulsed laser beam are set to keep the energy density below the optical breakdown threshold for ablation. Thus, the corneal tissue is processed with parameters of the pulsed laser beam set to cause a thermal effect in the corneal tissue rather than an optical breakdown effect for ablation.

BRIEF DESCRIPTION OF THE DRAWINGS

The present disclosure will be explained in more detail, by way of example, with reference to the drawings in which.

DETAILED DESCRIPTION

Figure 1:
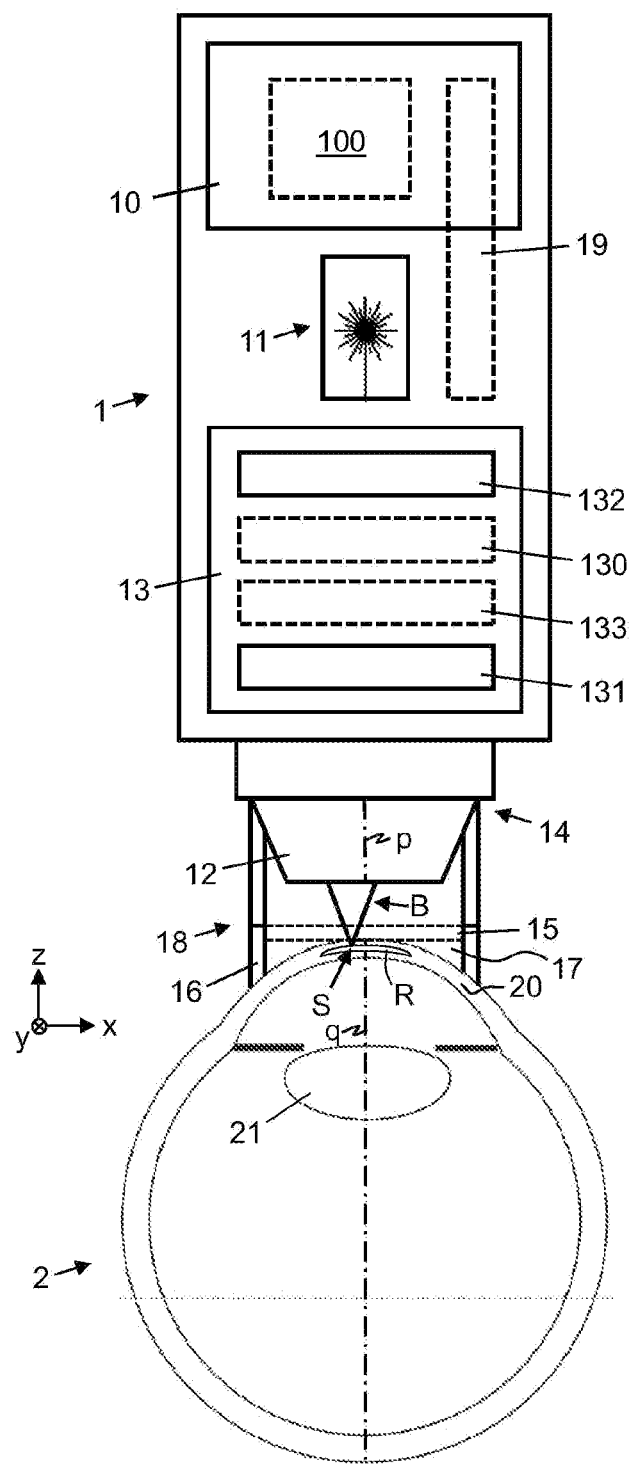
FIG. 1 shows a block diagram that schematically illustrates an ophthalmological device for refractive correction of a cornea with a pulsed laser beam, said device comprising a focusing optical module for focusing the pulsed laser beam in the cornea, and a scanner system for moving the focus to target locations in the cornea.

In FIG. 1, reference numeral 1 relates to an ophthalmological device for refractive correction of a cornea 20 of an eye 2 with a pulsed laser beam B.

Figure 13:
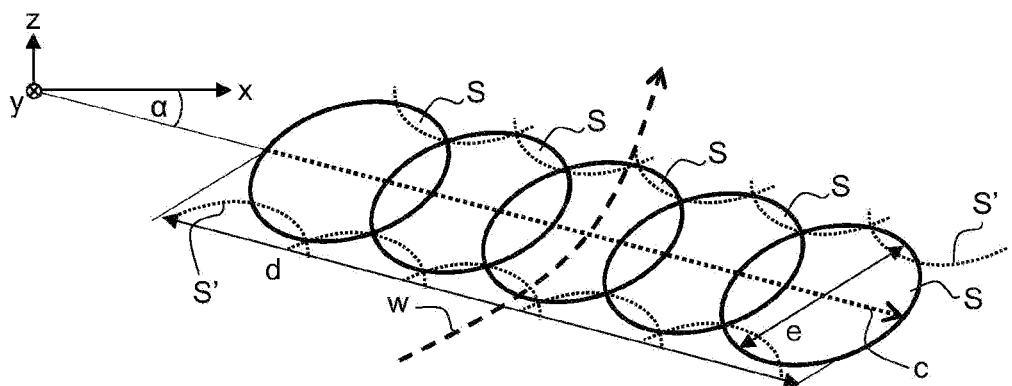
FIG. 13 shows a schematic top view of a scan line, running at an angle through a working line, with a series of partially overlapping focal spots moved by the scanner system along the scan line.
Figure 14:
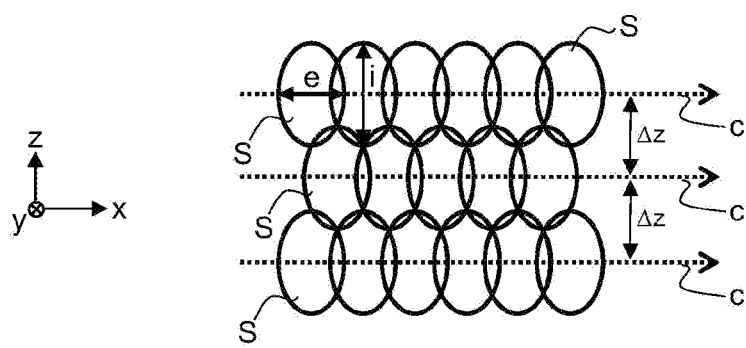
FIG. 14 shows a schematic cross-sectional view of superposed scan lines with focal spots moved by the scanner system along the scan line, whereby the focal spots partial overlap along the scan line and across the superposed scan lines.

As illustrated schematically in FIG. 1, the ophthalmological device 1 comprises a laser source 11 for generating the pulsed laser beam B, a focusing optical module 12 for focusing the pulsed laser beam B in the cornea 20 onto a focal spot S, and a scanner system 13 for moving the focal spot S to target locations in the cornea 20. FIGS. 13 and 14 illustrate schematically a series of partially overlapping focal spots S, S' with a spot diameter e typically in the range of 1 μm to 10 μm. It is pointed out here that the person skilled in the art will understand that a focal spot S refers to a laser interaction zone where tissue, here corneal tissue, is dissolved (ablated) to effect tissue cuts or volumetric tissue ablation. The extent of this zone or focal spot S, respectively, is in first approximation an ellipsoid with a length i (in z-direction or direction of projection p, respectively) and a diameter e (in the x/y-plane or normal to the z-direction or direction of projection p, respectively). Generally, the length i of a focal spot S is longer than its diameter e. Nevertheless, focusing optical modules with high numerical aperture may produce focal spots S with a more spherical shape where the length i corresponds to the diameter e. FIGS. 13 and 14 illustrate schematically, the partial overlapping of the focal spots S along the scan line c. FIG. 13 further illustrates schematically, the partial overlapping of the focal spots S of neighbouring scan lines c as indicated by focal spots S', depicted partially with dashed lines. FIG. 14, further illustrates schematically the partial overlapping of the focal spots S of superposed neighbouring scan lines c. The person skilled in the art will further understand that, as an alternative to separating (corneal) tissue by way of dissolving/ablating the tissue in the separation area, using partially overlapping focal spots S, S' and generating a cut surface or an ablation volume in the separation area, (corneal) tissue may also be separated by means of expanding gas bubbles, using non-overlapping and/or spatially separated focal spots, whereby expanding gas bubbles cause separation through tearing and/or cleavage of tissue but do not dissolve or ablate tissue.

In particular, the laser source 11 comprises a femtosecond laser for producing femtosecond laser pulses, which have pulse widths of typically 10 fs to 1000 fs (1 fs=$10^{-15}$ s). The laser source 11 is arranged in a separate housing or in a housing shared with the focusing optical module 12.

The focusing optical module 12 is configured to focus the pulsed laser beam B or the laser pulses, respectively, in the cornea 20 onto a focal spot S, i.e. for making the pulsed laser beam B converge to a focus or focal spot in the cornea 20. The focusing optical module 12 comprises one or more optical lenses. In an embodiment, the focusing optical module 12 comprises a focus adjustment device for setting the focal depth of the focal spot S, for example one or more movable lenses, in the focusing optical module 12 or upstream of the focusing optical module 12, or a drive for moving the entire focusing optical module 12 along the projection axis p (z-axis). By way of example, the focusing optical module 12 is installed in an application head 14, which can be placed onto the eye 2.

As illustrated schematically in FIG. 1, the ophthalmological device 1 comprises a patient interface 18 for attaching the application head 14 or the focusing optical module 12, respectively, onto the eye 2. Depending on the embodiment, the patient interface 18 is connected to the application head 14 in a fixed or removable manner.

The patient interface 18 comprises a contact body 15 and one or more suction elements configured to fix the contact body 15 and thus the patient interface 18 to the cornea 20. For example, the one or more suction elements are arranged in a fastening ring 16, e.g. a vacuum-controlled suction ring, whereby the one or more suction elements are connected fluidically to a suction pump. The contact body 15, also referred to as applanation body, is at least partly light-transparent.

Figure 2:
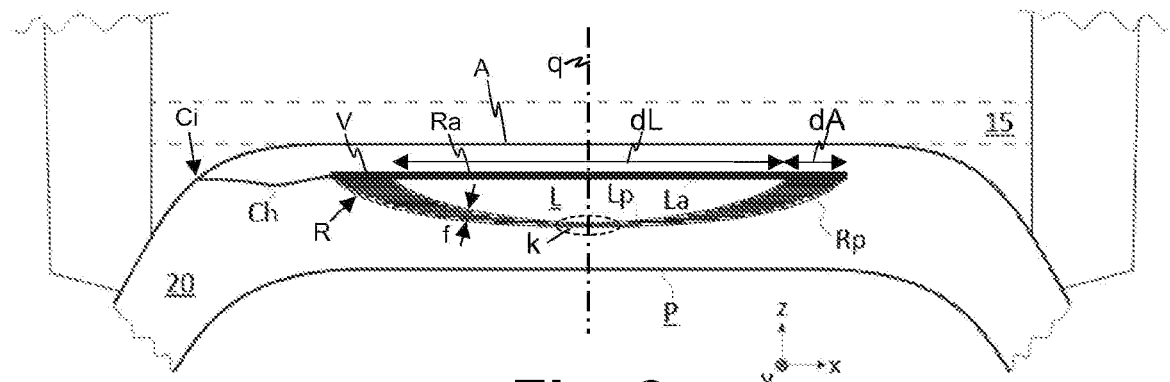
FIG. 2 shows a schematic cross-sectional view of a cornea in an applanated state with a void volume created in the cornea and a separated corneal tissue lenticule, to be removed through an incision in the cornea, to create the void volume required for a desired myopic refractive correction of the cornea.

As illustrated in FIG. 2, in the state where the patient interface 18 or the contact body 15, respectively, is fixed to the cornea 20, specifically to the exterior (anterior) surface A of the cornea 20, applanated is an applanation zone of the cornea 20, where the contact body 15 is in contact with the exterior (anterior) surface A of the cornea 20.

The scanner system 13 is configured to move the focal spot S to target locations in the cornea 20 by guiding and directing the pulsed laser beam B and thus the focal spot S to target locations in the cornea 20.

Figure 3:
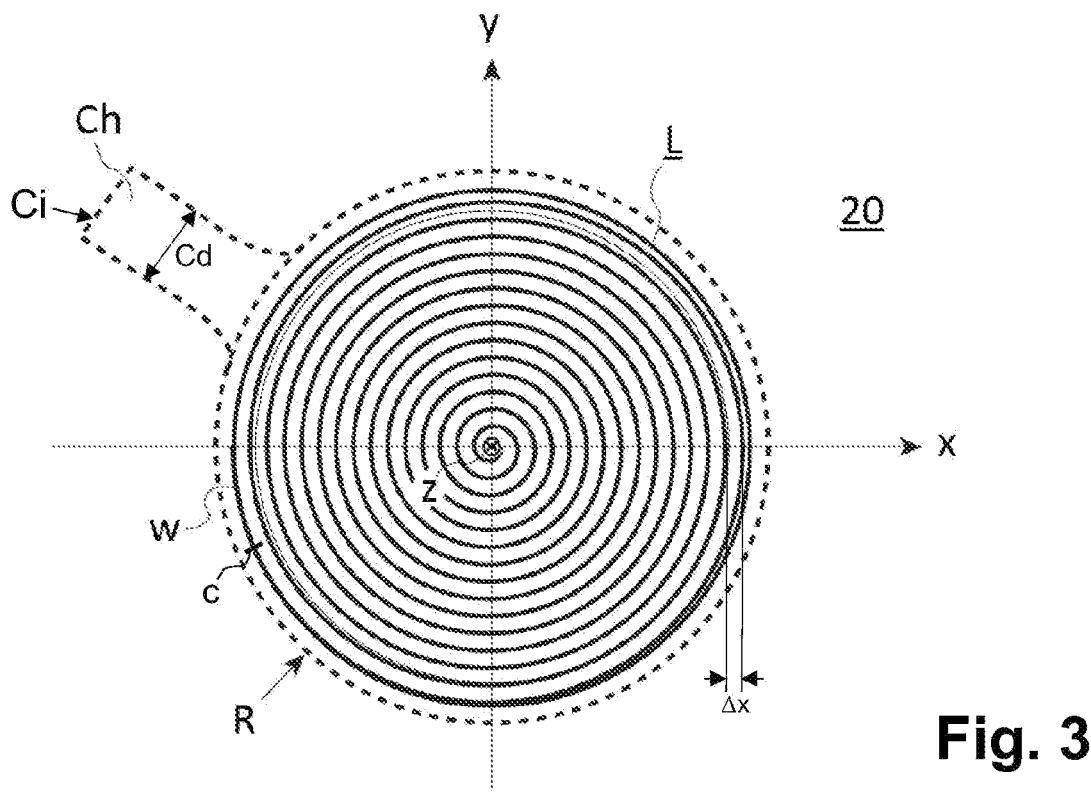
FIG. 3 shows a schematic top view of a cornea with a spiral shaped working line for creating a void volume in the cornea for a refractive correction of the cornea.
Figure 4:
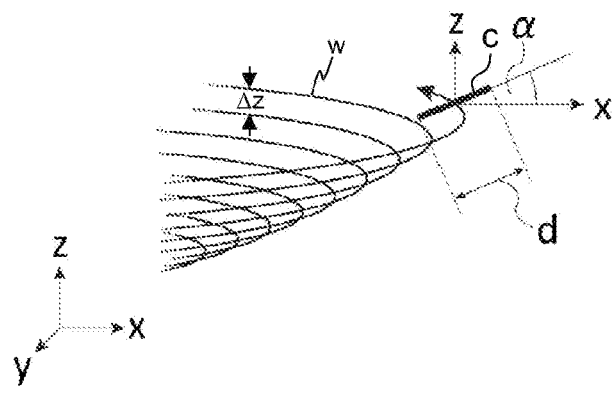
FIG. 4 shows a schematic three-dimensional view of a section of a spiral shaped working line for creating a void volume in the cornea for a refractive correction of the cornea.

The scanner system 13 comprises one or more scanner devices 131, also referred to as slow scanner device, configured to guide and direct the pulsed laser beam B and thus the focal spot S along a work line w, e.g. a spiral shaped work line, in a x/y-work-plane which is normal to a z-axis, whereby the z-axis is aligned with or essentially parallel to the projection axis p of the focusing optical module 12, as illustrated schematically in FIG. 1. Depending on the embodiment, the one or more scanner devices 131 comprise one or more actuators configured to move the focusing optical module 12 such that the focal spot S is moved along the work line w in the x/y-work-plane, and/or one or more deflection mirrors, each movable about one or two axes, configured to deflect the pulsed laser beam B and/or the laser pulses such that the focal spot S is moved along the work line w in the x/y-work-plane. To move the focal spot S along a work line w in the three-dimensional x/y/z-space, e.g. a spiral shaped work line w in the three-dimensional x/y/z-space, the one or more scanner devices 131 comprise one or more actuators configured to move the focusing optical module 12 or one or more of its optical lenses in z-direction, i.e. along the z-axis. FIG. 3 illustrates schematically in top view a spiral shaped working line w in the cornea 20. FIG. 4 shows a schematic three-dimensional view of a section of a spiral shaped working line w in the cornea 20.

The scanner system 13 comprises a further scanner device 132, also referred to as fast scanner device, configured to guide and direct the pulsed laser beam B and thus the focal spot S along a scan line c at a scanning speed that is comparatively faster than the scanning speed of the aforementioned slow scanner device 131. For example, the fast scanner device 132 comprises a polygon scanner. The fast scanner device 132 is configured to move the focal spot S, overlaid on the movement along the work line w, along a scan line c that runs through the work line w, at an angle to the work line w, as illustrated in FIGS. 3, 4, and 13.

The scanner system 13 further comprises a divergence-modulator 133, also referred to as z-modulator, configured to move the focal spot S along the z-axis which is aligned with or essentially parallel to the projection axis p of the focusing optical module 12. The divergence modulator 133 is configured to dynamically change the divergence of the pulsed laser beam B. As illustrated schematically in FIGS. 4 and 13, the combined (synchronized) movement of the focal spot S by the aforementioned fast scanner device 132 and by the divergence-modulator 133 constitutes a movement of the focal spot S along a scan line c which is bent and/or tilted with a tilting angle α from the x/y-plane.

In an embodiment, the scanner system 13 further comprises a length modulator 130 configured to modulate the length d, d1, d2 of the scan line c. For example, the length modulator 130 comprises an adjustable shutter device arranged downstream of the fast scanner device 132. As illustrated schematically in FIG. 13, the length d of the scan line c is adjusted by controlling the length modulator 130, e.g. the shutter device, to let through a set number of laser pulses from the fast scanner device 132 for producing a corresponding number of focal spots S.

As illustrated in FIG. 4, the synchronized combination of the movement of the focal spots S along the working line w in the x/y/z-space by the slow scanner device 131, with the overlaid movement of the focal spots S along the scan line c by the fast scanner device 132, and the tilting of the scan line c with a tilting angle α from the x/y-plane by the divergence-modulator 133, and optionally the adjustment of the length d of the scan line c by the length modulator 130, makes it possible not only to generate plane or curved cut surfaces inside the cornea 20, but also to perform with great flexibility volumetric ablation of corneal tissue. For example, volumetric ablation is achieved inside the cornea 20 by driving the scan line c overlaid on the work line w with a continuous increase Δz in z-direction (per cycle) to generate superposed ablation layers with partially overlapping focal spots S along the scan line c (as illustrated in FIG. 13) and among adjacent superposed ablation layers.

Various further and more specific embodiments of the scanner system 13 are described by the applicant in patent applications US 2019/0015250, US 2019/0015251, and US 2019/0015253 which are hereby incorporated by reference.

The ophthalmological device 1 further comprises an electronic circuit 10 for controlling the laser source 11 and the scanner system 13. The electronic circuit 10 implements a programmable control device and comprises e.g. one or more processors 100 with program and data memory and programmed software modules for controlling the processors 100, and/or other programmable circuits or logic units such as ASICs (application specific integrated circuits).

In an embodiment, the ophthalmological device 1 further comprises a measurement system 19 configured to determine positional reference data of the cornea 20. Depending on the embodiment, the measurement system 19 comprises a video capturing system, an optical coherence tomography (OCT) system, and/or a structured light illumination system. Accordingly, the measurement data or positional reference data determined by the measurement system 19 includes video data, including top view data (comprising two-dimensional images), and/or OCT data of the cornea 20 (comprising three-dimensional tomography data). The measurement system 19 is configured to determine the positional reference data of the cornea 20 also in an applanated state of the cornea 20. The measurement system 19 is connected to and/or integrated with the electronic circuit 10 which is further configured to control the scanner system 13, using the positional reference data from the measurement system 19.

The electronic circuit 10 is configured to control the scanner system 13 to move the focal spot S inside the cornea 20 to generate for refractive correction of a cornea 20 a void volume R inside the cornea 20. More specifically, as illustrated schematically in FIG. 2, the electronic circuit 10 is configured to control the scanner system 13 to move the focal spot S inside the cornea 20 to generate the void volume R inside the cornea 20 with multiple volumetric parts whereby at least one first volumetric part V of the void volume R is generated by ablating the cornea tissue inside the first volumetric part V and at least one second volumetric part L of the void volume R is generated as an integral piece of cornea tissue to be removed from the void volume R through one or more incisions Ch in the cornea 20.

As illustrated schematically in FIGS. 2 and 5-12, the electronic circuit 10 is configured to control the scanner system 13 to move the focal spot S inside the cornea 20 to generate the ablated first volumetric part V by ablating the cornea tissue inside the first volumetric part V with a thickness f of at least two focal spots S. In other words, the ablated first volumetric part V is generated with a thickness of at least two superposed scan lines c or layers of focal spots S in z-direction (or direction of projection p), and at least two partially overlapping focal spots S in x-direction and y-direction (or in a plane normal to the direction of projection p). Thus, the thickness f of the ablated first volumetric part V is at least two times the diameter e of a focal spot S (see FIGS. 13 and 14). The person skilled in the art will understand that an ablated (three-dimensional) volume V has a thickness f of at least two focal spots S in x-, y-, and z-direction, whereas a cut surface has a thickness of just one focal spot S, i.e. one diameter e of a focal spot S. For typical human eyes, the separated piece of cornea tissue L constituting the second volumetric part L of the void volume R has a width dL (diameter) in the range of 4.5 mm to 7.5 mm; the width dA (in the x/y-plane) of the ablated first volumetric part V is in the range of 50 μm to 1 mm. The overall width (diameter) of the void volume R is thus in the range of approximately 4.5 mm to 9.5 mm.

As is further illustrated schematically in FIGS. 2 and 5-12, the electronic circuit 10 is configured to control the scanner system 13 to move the focal spot S inside the cornea 20 to generate the second volumetric part L of the void volume R by separating it from the surrounding cornea tissue. At least a part of the second volumetric part L is separated from the cornea 20 by the ablated first volumetric part V. Thus, at least a part of the second volumetric part L of the void volume R, or more specifically of the piece of corneal tissue L to be removed from the cornea, is shaped by ablating the ablated first volumetric part V.

Figure 9:
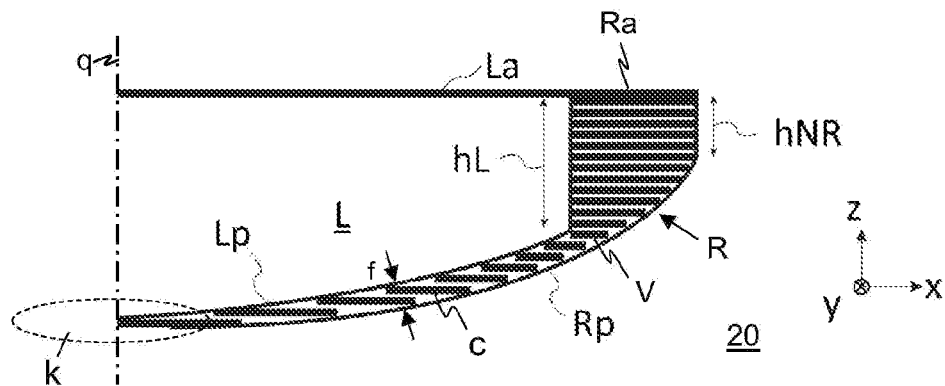
Figure 10:
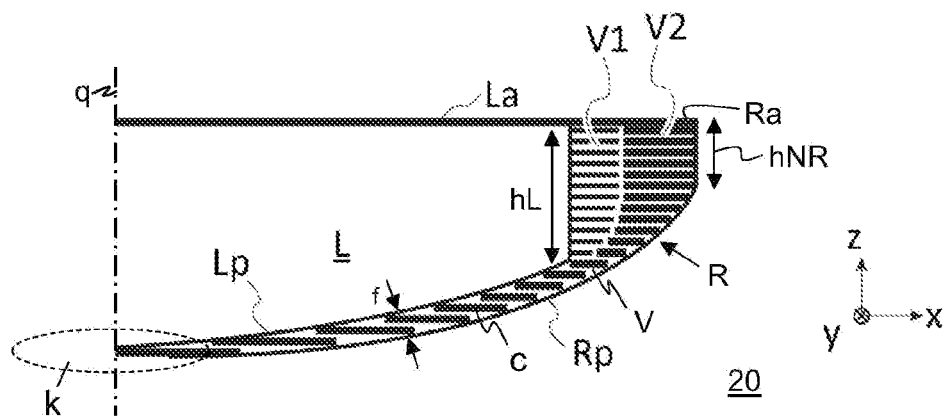
Figure 11:
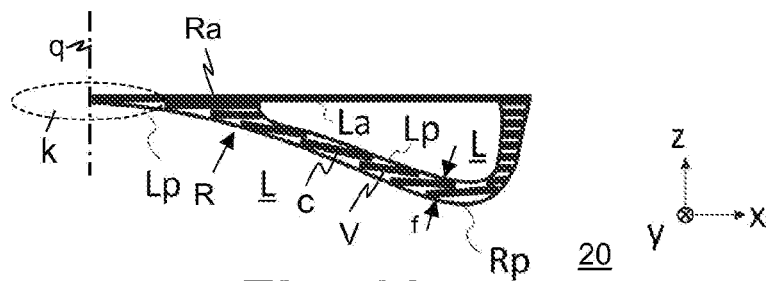
FIGS. 11-12 show schematic cross-sectional views of a cornea in an applanated state with a half section of a void volume created in the cornea and a separated half section of a corneal tissue lenticule, to be removed through an incision in the cornea, to create the void volume required for a desired hyperopic refractive correction of the cornea.
Figure 12:
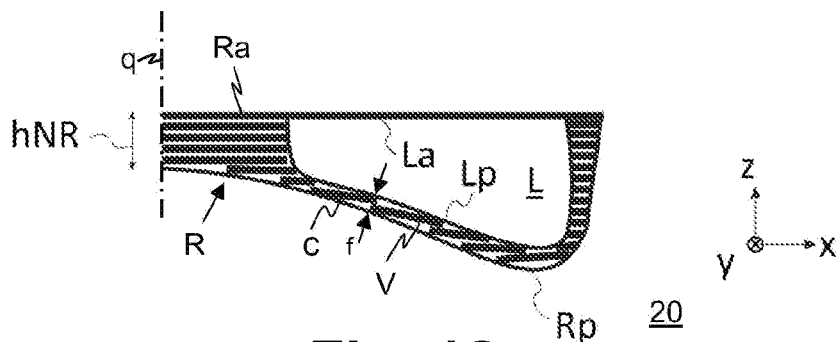

In the following paragraphs, different configurations of the void volume R and respective ablated first volumetric part V and separated second volumetric part L are described with reference to FIGS. 2-12, whereby FIGS. 2 and 5-10 show cross-sectional views of void volumes R for a desired myopic refractive correction of the cornea 20, and FIGS. 11 and 12 show cross-sectional views of void volumes R for a desired hyperopic refractive correction of the cornea 20. For the sake of clarity, it is pointed out here that the electronic circuit 10 is configured to control the scanner system 13 to move the focal spot S to generate the void volumes R in the cornea 20 to produce one or more of these configurations and combinations thereof, for example, as selected or selectable by an operator. Furthermore, it is pointed out that only FIG. 2 shows a cross-sectional view of a complete void volume R whereas FIGS. 5-12 show cross-sectional views of only half of the void volume R but could be mirrored on the symmetry axis q for completeness.

Generating the void volume R in one part by ablating corneal tissue and in another part by removing a separated piece of corneal tissue from the cornea 20 makes it possible to generate the void volume with a reduced risk of tears and frayed edges of the separated piece of corneal tissue L to be removed, while keeping the size of the void volume R small to avoid unnecessary weakening of the cornea 20. This is accomplished by avoiding fragile and instable thinness of the separated piece of corneal tissue L to be removed, e.g. a lenticule or a ring, by ablating the corneal tissue in narrow areas of the void volume R, i.e. by dissolving the corneal tissue. Any thin or narrow area or region of the void volume R, as planned for a desired refractive correction, which has a diameter or thickness (with regards to its anterior volume surface Ra and its posterior volume surface Rp) smaller than a defined (maximum) thinness threshold, will be generated by ablating the entire corneal tissue in this area or region of the void volume R, without removing any corneal tissue from this area or region of the void volume R. For example, the thinness threshold is set to a thickness in the range of the thickness of two to three lamely (collagen layers), which corresponds to a thinness threshold in the range of approximately 4 μm to 6 μm. In other words, any area of the void volume R which has a thickness smaller than a defined thinness threshold, is generated by ablating the entire corneal tissue in this area, without extracting any corneal tissue from this area. Thereby, the void volume R can be generated with areas of thinness, as desired/required for the refractive correction, by dissolving the corneal tissue in these areas, but without generating the piece of corneal tissue L to be removed from the cornea 20 with undesirable, fragile, instable thin areas. Thus, for a desired myopic refractive correction of the cornea 20 the narrow (thin) peripheral rim area of the void volume R is generated by way of volumetric ablation, whereby for the sake of clarity it is pointed out that the peripheral rim area of the void volume R is the region of the void volume R most distant from the central symmetry axis q. For a desired hyperopic refractive correction of the cornea 20 the narrow (thin) interior area of the void volume R is generated by way ablating a simple cut surface and/or an ablation volume, whereby for the sake of clarity it is pointed out that the interior area of the void volume R is the region of the void volume R surrounding the central symmetry axis q. In either case, the piece of corneal tissue L separated for removal from the cornea 20 remains stable, without any undesirable, fragile, instable thin areas.

As illustrated in FIGS. 2 and 5-12, the void volume R is determined by the anterior volume surface Ra of the void volume R, facing the exterior/anterior surface A of the cornea 20, and the posterior volume surface Rp of the void volume R, facing the posterior surface P of the cornea 20.

As further illustrated in FIGS. 2 and 5-12, the second volumetric part L of the void volume R, separated as an integral piece of cornea tissue, e.g. in form of a lenticule L (FIGS. 2 and 5-12) or a ring (FIGS. 11 and 12), is determined by an anterior surface La, e.g. anterior lenticule (or ring) surface La, facing the exterior/anterior surface A of the cornea 20, and posterior surface Lp, e.g. a posterior lenticule (or ring) surface Lp, facing the posterior surface P of the cornea 20.

In the scenarios illustrated in FIGS. 2 and 5-12, the anterior surface La of the separated piece of cornea tissue, e.g. the anterior lenticule (or ring) surface La, is generated by ablating a cut surface performed to separate the piece of cornea tissue L, e.g. the lenticule L (FIGS. 2 and 5-12) or the ring L (FIGS. 11 and 12), from the anterior volume surface Ra of the void volume R. For example, the cut surface for the anterior lenticule (or ring) surface La is generated by the electronic circuit 10 controlling the scanner system 13 to move the focal spot S inside the cornea 20 along a spiral work line w, as illustrated in top view in FIG. 3, keeping a constant work height, i.e. maintaining z constant ($\Delta z=0$), without any tilting angle of the scan line c ($\alpha=0$), and keeping the length d of the scan line c at a constant length which corresponds to the distance between two spiral arms ($d=\Delta x$).

In the scenarios illustrated in FIGS. 2 and 5-12, the posterior surface Lp of the separated piece of cornea tissue, e.g. the posterior lenticule (or ring) surface Lp, is generated as a result of ablating the first volumetric part V of the void volume R. As indicated in FIGS. 2 and 5-10, depending on the embodiment and/or configuration, the lowest area k of the separated piece of cornea tissue L, e.g. the lenticule L, is separated from the posterior surface Rp of the void volume R by ablating a cut surface, with a thickness of just one focal spot S, or by volumetric ablation with a thickness f of more than one focal spot S.

Figure 5:
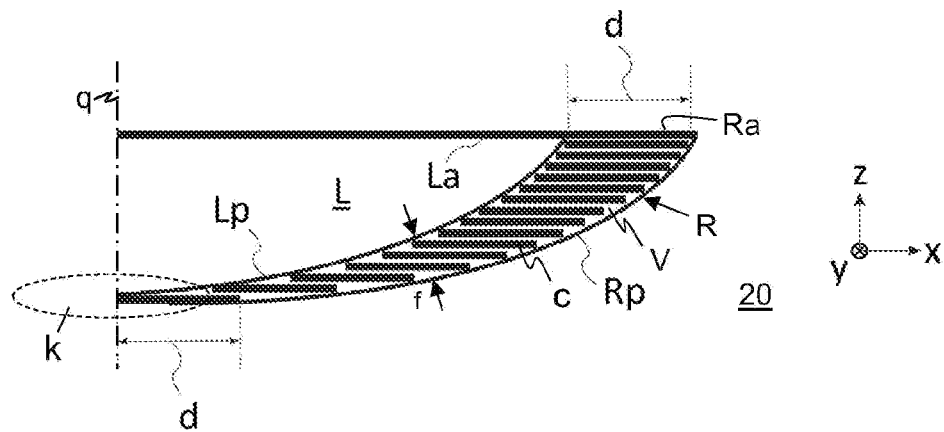
FIGS. 5-10 show schematic cross-sectional views of a cornea in an applanated state with a half section of a void volume created in the cornea and a separated half section of a corneal tissue lenticule, to be removed through an incision in the cornea, to create the void volume required for a desired myopic refractive correction of the cornea.
Figure 6:
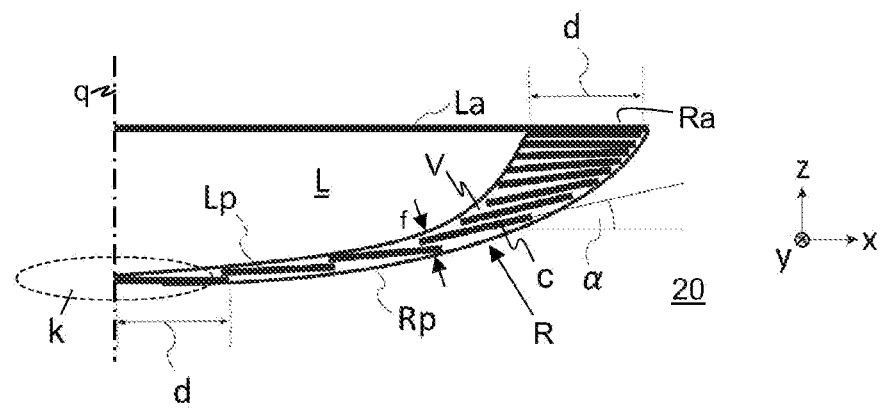

In the scenarios illustrated in FIGS. 2, 5, and 6, the separated piece of cornea tissue L is shaped by the ablation of the first volumetric part V of the void volume R in the form of a lenticule L with a curved peripheral rim that ends in a corner where the posterior lenticule surface Lp meets the anterior lenticule surface La. In these scenarios, the scan line c has an unchanged, constant length d. In the scenario illustrated in FIG. 6, the scan line c is tilted with a tilting angle α to adapt to the curvature of the posterior lenticule surface Lp and/or the posterior surface Rp of the void volume R.

Figure 7:
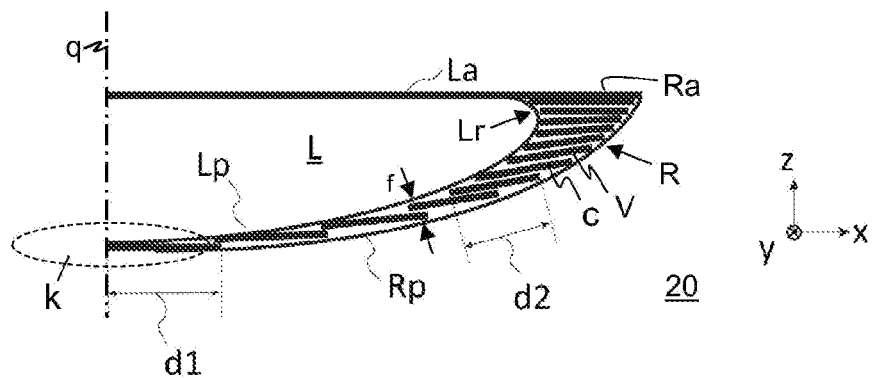

In the scenario illustrated in FIG. 7, the separated piece of cornea tissue L is shaped by the ablation of the first volumetric part V of the void volume R in the form of a lenticule L with a rounded peripheral rim Lr where the posterior lenticule surface Lp transitions to the anterior lenticule surface La. In this scenario, the length d1, d2 of the scan line c as well as the tilting angle α of the scan line c are changed to adapt to the curvature of the posterior lenticule surface Lp and/or the posterior surface Rp of the void volume R.

Figure 8:
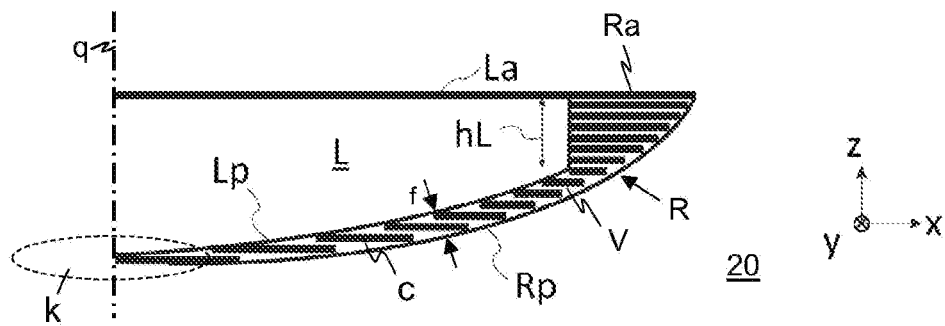

In the scenarios illustrated in FIGS. 8-10, the separated piece of cornea tissue L is shaped by the ablation of the first volumetric part V of the void volume R in the form of a lenticule L with a peripheral rim that has a vertical wall hL (running straight in z-direction). The height of the vertical wall hL of the lenticule L is in the range of 15-60 µm. In the scenarios of FIGS. 9 and 10, the peripheral rim of the void volume R has a vertical wall hNR (running straight in z-direction). As illustrated in FIGS. 8-10, the length d of the scan line c is changed to adapt to the shapes of the lenticule L and the posterior surface Rp of the void volume R. The height of the vertical wall hNR of the void volume R is in the range of 10-40 µm.

In the scenario illustrated in FIG. 10, the area of the void volume R, between the vertical wall hL of the lenticule L and the vertical wall hNR of the void volume R, is processed with different parameters of the pulsed laser beam B. More specifically, in the region V1, adjacent to the vertical wall hL of the lenticule L, different parameters of the pulsed laser beam B are used than in the region V2, adjacent to vertical wall hNR of the void volume R. The region V1 adjacent to the vertical wall hL of the lenticule L is processed with parameters of the pulsed laser beam B, including pulse energy, pulse overlap, pulse rate, pulse duration, and/or focal spot size of the pulsed laser beam B, which are set to fuse the corneal tissue at the peripheral rim hL of the lenticule L rather than to dissolve the corneal tissue. More specifically, the parameters of the pulsed laser beam B are set to keep the energy density below the optical breakdown threshold of the tissue for ablation. The region V1 is processed with parameters of the pulsed laser beam B set to cause a thermal effect in the corneal tissue to heat the corneal tissue in region V1 to above 60° C., preferably to approximately 75° but possibly even higher up to 90° C. At these temperatures corneal collagen starts to denaturise (denaturation effect) and corneal lamellæ are fused together after cooldown. The region V2 adjacent to vertical wall hNR of the void volume R is processed with parameters of the pulsed laser beam B, including pulse energy, pulse overlap, pulse rate, pulse duration, and/or focal spot size of the pulsed laser beam B, which are set to dissolve the corneal tissue such as to perform volumetric ablation of the corneal tissue in this region V2. More specifically, the parameters of the pulsed laser beam B are set to keep the energy density at or above the optical breakdown threshold for ablation (e.g. at approximately 0.5 J/cm$^2$ to 1 J/cm$^2$ energy density of a single pulse). The region V2 is processed with parameters of the pulsed laser beam B set to cause ablation of the corneal tissue.

In the scenarios illustrated in FIGS. 11 and 12, the separated piece of cornea tissue L is shaped by the ablation of the first volumetric part V of the void volume R in the form of a ring L, with a peripheral rim and an interior rim, resembling the shape of a donut. In the scenario of FIG. 12, the central area (around the symmetry axis q), i.e. the interior of the ring or the whole of the donut, is ablated with a defined height hNR (in z-direction) in the range of 10-40 µm. In the scenario of FIG. 11, in the central area k, the anterior surface Ra of the void volume R and the posterior surface Rp of the void volume R are merely separated by ablating a cut surface, with a thickness of just one focal spot S. As illustrated in FIGS. 11 and 12, the peripheral (outer) rim of the ring L is shaped by the ablation of the first volumetric part V of the void volume R and by changing the length d of the scan line c to define the shape of the peripheral rim of the ring L and adapt to the posterior surface Rp of the void volume R. Likewise the interior rim of the ring L is shaped by the ablation of the first volumetric part V of the void volume R and by changing the length d of the scan line c to define the shape of the interior rim of the ring L and adapt to the posterior surface Rp of the void volume R. The posterior surface Lp of the ring L, facing the symmetry axis q, is shaped by the ablation of the first volumetric part V of the void volume R and by changing the length d of the scan line c as well as the tilting angle α of the scan line c to define the shape of the posterior surface Lp of the ring L and adapt to the posterior surface Rp of the void volume R.

The electronic circuit 10 is further configured to control the scanner system 13 to move the focal spot S to cut in the cornea 20 one or more "mechanical" extraction channels Ch, as illustrated in FIGS. 2 and 3. As illustrated, an extraction channel Ch comprises an extraction incision Ci in the exterior (anterior) surface A of the cornea 20. The extraction channel Ch connects the void volume R to the extraction incision Ci and enables mechanical extraction of the separated piece of cornea tissue L, e.g. the lenticule L or the ring L, from the cornea 20 through the extraction incision Ci to the exterior of the cornea 20. The mechanical extraction channel Ch has a channel width Cd in the range of 2 mm to 5 mm.

The invention claimed is:

1. An ophthalmological device for refractive correction of a cornea of an eye by generating a three-dimensional void volume inside the cornea, the ophthalmological device comprising:

a laser source configured to generate a pulsed laser beam;

a focusing optical module configured to make the pulsed laser beam converge onto a focal spot in the cornea;

a scanner system configured to move the focal spot to target locations in the cornea; and an electronic circuit configured to control the scanner system to move the focal spot inside the cornea to generate an ablated first part of the void volume by ablating cornea tissue, without extracting the corneal tissue, with a thickness of more than one focal spot in direction of any of the three dimensions inside the first part of the void volume, to generate a separated second part of the void volume by separating the second part of the void volume as piece of cornea tissue to be removed from the void volume through an incision in the cornea, and to include in the first part of the void volume any area of the void volume, planned for a desired refractive correction, which has a thickness smaller than a defined thinness threshold, with respect to a distance between an anterior volume surface and a posterior volume surface, wherein the piece of cornea tissue is shaped by ablating the first part and at least a part of the separated second part is separated from the cornea by the ablated first part.

2. The ophthalmological device of claim 1, wherein the electronic circuit is configured to control the scanner system to move the focal spot inside the cornea to ablate the cornea tissue in the first part of the void volume and generate the piece of cornea tissue in the second part of the void volume in shape of a lenticule.

3. The ophthalmological device of claim 1, wherein the electronic circuit is configured to control the scanner system to move the focal spot inside the cornea to ablate the cornea tissue in the first part of the void volume and generate the piece of cornea tissue in the second part of the void volume with a ring shape.

4. The ophthalmological device of claim 1, wherein the electronic circuit is configured to control the scanner system to move the focal spot inside the cornea to ablate the cornea tissue in the first part of the void volume and thereby shape the piece of cornea tissue in the second part of the void volume with a rounded rim.

5. The ophthalmological device of claim 1, wherein the electronic circuit is configured to control the scanner system to move the focal spot inside the cornea to ablate the cornea tissue in the first part of the void volume and thereby shape the piece of cornea tissue in the second part of the void volume with a rim having a straight wall in direction of an optical axis of the focusing optical module.

6. The ophthalmological device of claim 1, wherein the electronic circuit is configured to control the scanner system to move the focal spot inside the cornea to ablate the cornea tissue in the first part of the void volume and thereby shape the ablated first part of the void volume with a rim having a straight wall in direction of an optical axis of the focusing optical module.

7. The ophthalmological device of claim 1, wherein the ophthalmological device further comprises a patient interface with a contact body, which contact body brings an exterior surface of the cornea in an applanated form in a state where the patient interface is applied on the cornea; and the electronic circuit is configured to control the scanner system to move the focal spot inside the cornea to generate the anterior volume surface of the void volume equidistant to the exterior surface of the cornea.

8. The ophthalmological device of claim 1, wherein the scanner system comprises a first scanner device configured to move the focal spot with a first scanning speed to target locations along a working line, and a second scanner device configured to move the focal spot with a second scanning speed, comparatively faster than the first scanning speed, to target locations along a scan line which runs through the working line at an angle to the working line; and the electronic circuit is configured to control the first scanner device to move the focal spot to target locations along a spiral shaped working line inside the cornea, and to control the second scanner device to move the focal spot to target locations along the scan line to ablate the cornea issue and generate the ablated first part of the void volume.

9. The ophthalmological device of claim 8, wherein the scanner system comprises a divergence modulator configured to modulate a divergence of the pulsed laser beam for adjusting a location of the focal spot along an optical axis of the focusing optical module and tilting the scan line in direction of the optical axis; and the electronic circuit is configured to control the divergence modulator to adjust a tilting angle of the scan line with respect to a shape of at least one of: the ablated first part or the separated second part.

10. The ophthalmological device of claim 8, wherein the scanner system comprises a length modulator configured to modulate a length of the scan line; and the electronic circuit is configured to control the length modulator to adjust the length of the scan line with respect to a shape of at least one of: the ablated first part or the separated second part.

11. The ophthalmological device of claim 1, wherein the electronic circuit is configured to control the laser source to adjust one or more parameters of the pulsed laser beam for ablating different regions of the ablated first part with different parameters of the pulsed laser beam, the one or more parameters of the pulsed laser beam including at least one of: pulse energy, pulse overlap, pulse rate, pulse duration, or focal spot size.

12. The ophthalmological device of claim 1, wherein the electronic circuit is configured to control the laser source to adjust one or more parameters of the pulsed laser beam for processing a region of corneal tissue adjacent to at least part of the outer surface of the piece of cornea tissue to be removed from the void volume to fuse the corneal tissue of the part of the outer surface of the piece of cornea tissue to be removed from the void volume, the one or more parameters of the pulsed laser beam including at least one of: pulse energy, pulse overlap, pulse rate, pulse duration, or focal spot size.

13. A computer program product comprising a non-transitory computer-readable medium having stored thereon computer program code for controlling a processor of an ophthalmological device for refractive correction of a cornea of an eye by generating a three-dimensional void volume inside the cornea, which ophthalmological device comprises a laser source configured to generate a pulsed laser beam, a focusing optical module configured to make the pulsed laser beam converge onto a focal spot in the cornea, and a scanner system configured to move the focal spot to target locations in the cornea, whereby the computer program code is configured to control the processor such that the processor:

directs the scanner system to move the focal spot inside the cornea to generate an ablated first part of the void volume by ablating cornea tissue, without extracting the corneal tissue, with a thickness of more than one focal spot in direction of any of the three dimensions inside the first part of the void volume, to generate a separated second part of the void volume by separating the second part of the void volume as piece of cornea tissue to be removed from the void volume through an incision in the cornea, and to include in the first part of the void volume any area of the void volume, planned for a desired refractive correction, which has a thickness smaller than a defined thinness threshold, with respect to a distance between an anterior volume surface and a posterior volume surface, wherein the piece of cornea tissue is shaped by ablating the first part and at least a part of the separated second part is separated from the cornea by the ablated first part.

14. A method comprising:
generating a pulsed laser beam;
making the pulsed laser beam converge onto a focal spot in a cornea of an eye;
moving the focal spot to target locations in the cornea;
moving the focal spot inside the cornea to generate an ablated first part of a void volume by ablating cornea tissue, without extracting the corneal tissue, with a thickness of more than one focal spot in direction of any of three dimensions inside the first part of the void volume; and
generating a separated second part of the void volume by separating the second part of the void volume as a piece of cornea tissue to be removed from the void volume through an incision in the cornea,
wherein included in the first part of the void volume is any area of the void volume, planned for a desired refractive correction, which has a thickness smaller than a defined thinness threshold, with respect to a distance between an anterior volume surface and a posterior volume surface, and
wherein the piece of cornea tissue is shaped by ablating the first part and at least a part of the separated second part is separated from the cornea by the ablated first part.

* * * * *